(12) United States Patent
Barbarossa et al.

(10) Patent No.: US 8,472,031 B2
(45) Date of Patent: Jun. 25, 2013

(54) APPARATUS AND METHOD FOR OPTICAL INTERROGATION

(75) Inventors: Giovanni Barbarossa, Saratoga, CA (US); Yan Zhou, Pleasanton, CA (US)

(73) Assignees: Valerio Pruneri, Castelldefels-Barcelona (ES); Marc Jofre Cruanyes, Canet de Mar-Barcelona (ES)

(*) Notice: Subject to any disclaimer, the term of this patent is extended or adjusted under 35 U.S.C. 154(b) by 356 days.

(21) Appl. No.: 12/800,873

(22) Filed: May 25, 2010

(65) Prior Publication Data
US 2011/0292401 A1 Dec. 1, 2011

(51) Int. Cl.
*G01B 9/02* (2006.01)

(52) U.S. Cl.
USPC .......................... 356/520; 356/491

(58) Field of Classification Search
USPC .............. 356/453, 491, 517, 520; 359/370, 359/371
See application file for complete search history.

(56) References Cited

U.S. PATENT DOCUMENTS

| | | | |
|---|---|---|---|
| 5,604,591 A * | 2/1997 | Kitagawa | 356/491 |
| 5,623,561 A | 4/1997 | Hartman | |
| 5,955,729 A | 9/1999 | Nelson et al. | |
| 6,128,127 A * | 10/2000 | Kusaka | 359/371 |
| 6,594,011 B1 | 7/2003 | Kempen | |
| 6,833,920 B2 | 12/2004 | Rassman et al. | |
| 6,992,777 B2 * | 1/2006 | Han et al. | 356/491 |
| 7,094,595 B2 | 8/2006 | Cunningham et al. | |
| 7,233,396 B1 | 6/2007 | Hall et al. | |
| 7,349,590 B2 | 3/2008 | Mozdy | |
| 7,586,616 B2 | 9/2009 | Ran et al. | |
| 2008/0068615 A1 | 3/2008 | Striemer et al. | |

FOREIGN PATENT DOCUMENTS

JP        2004061614 A  *  2/2004

* cited by examiner

*Primary Examiner* — Michael A Lyons
(74) *Attorney, Agent, or Firm* — Gary J. Gershik; Cooper & Dunham LLP

(57) ABSTRACT

An interrogation apparatus and method use a partial shear optical interference apparatus to interrogate the optical properties of an array of target specimen probe volumes as compared to an array of reference sample probe volumes. The apparatus produces a formatted probe beam that contains a partially sheared probe beam pair that is formatted into an array of completely sheared probe beam pairs. Target specimen probe volumes and reference sample probe volumes are suitably organized and exposed to the array of completely sheared probe beam pairs.

18 Claims, 19 Drawing Sheets

BC = Birefringent crystal
E = Extraordinary
O = Ordinary

|   |   |   |   |   |   |   |
|---|---|---|---|---|---|---|
|   | S(5,1) | S(5,2) | S(5,3) | S(5,4) | S(5,5) |   |
|   | S(4,1) | S(4,2) | S(4,3) | S(4,4) | S(4,5) |   |
|   | S(3,1) | S(3,2) | S(3,3) | S(3,4) | S(3,5) |   |
|   | S(2,1) | S(2,2) | S(2,3) | S(2,4) | S(2,5) |   |
|   | S(1,1) | S(1,2) | S(1,3) | S(1,4) | S(1,5) |   |
|   |   |   |   |   |   |   |

Fig. 8

|   |   |   |   |   |   |   |
|---|---|---|---|---|---|---|
|   |   | EO(5,1) | EO(5,2) | EO(5,3) | EO(5,4) | EO(5,5) |
|   | OE(5,1) | OE(5,2) + EO(4,1) | OE(5,3) + EO(4,2) | OE(5,4) + EO(4,3) | OE(5,5) + EO(4,4) | EO(4,5) |
|   | OE(4,1) | OE(4,2) + EO(3,1) | OE(4,3) + EO(3,2) | OE(4,4) + EO(3,3) | OE(4,5) + EO(3,4) | EO(3,5) |
|   | OE(3,1) | OE(3,2) + EO(2,1) | OE(3,3) + EO(2,2) | OE(3,4) + EO(2,3) | OE(3,5) + EO(2,4) | EO(2,5) |
|   | OE(2,1) | OE(2,2) + EO(1,1) | OE(2,3) + EO(1,2) | OE(2,4) + EO(1,3) | OE(2,5) + EO(1,4) | EO(1,5) |
|   | OE(1,1) | OE(1,2) | OE(1,3) | OE(1,4) | OE(1,5) |   |

Fig. 9

|        |        |        |        |        |
|--------|--------|--------|--------|--------|
| C(5,1) | C(5,2) | C(5,3) | C(5,4) | C(5,5) |
| C(4,1) | C(4,2) | C(4,3) | C(4,4) | C(4,5) |
| C(3,1) | C(3,2) | C(3,3) | C(3,4) | C(3,5) |
| C(2,1) | C(2,2) | C(2,3) | C(2,4) | C(2,5) |
| C(1,1) | C(1,2) | C(1,3) | C(1,4) | C(1,5) |

Fig. 10

|        |        |        |        |        |
|--------|--------|--------|--------|--------|
| D(5,1) | D(5,2) | D(5,3) | D(5,4) | D(5,5) |
| D(4,1) | D(4,2) | D(4,3) | D(4,4) | D(4,5) |
| D(3,1) | D(3,2) | D(3,3) | D(3,4) | D(3,5) |
| D(2,1) | D(2,2) | D(2,3) | D(2,4) | D(2,5) |
| D(1,1) | D(1,2) | D(1,3) | D(1,4) | D(1,5) |

APPARATUS AND METHOD FOR OPTICAL INTERROGATION

FIELD OF THE INVENTION

The invention relates to apparatuses and methods for interrogating the optical properties of an array of probe volumes.

BACKGROUND OF THE INVENTION

The refractive index of a probe volume is in general a complex number comprising a real part and an imaginary part which both depend on the space coordinates. The complex spatial distribution of the refractive index of a probe volume is referred to here as the "optical properties" of that probe volume.

There is a need for interrogating the optical properties of an array of probe volumes in a variety of applications including Biomedical Diagnostics, Genomics, Proteomics, Drug Discovery, DNA Sequencing, Optical Data Storage, Material Science, Occupational Health and Safety, Civilian or Military Counterterrorism, Battlefield, Electrophoresis, Analytical Chromatography, Semiconductor Processing, Metrology, Counterfeiting, Food Processing, Forensics, Law Enforcement, Environmental Monitoring, Microscopy, Mass Spectroscopy, Microfluidic Dynamics, and Flow Cytometry. In many of these applications the optical properties of a probe volume that includes a sample of a material of interest (target specimen probe volume) are compared with the optical properties of a probe volume including a sample of a material of reference (reference sample probe volume). Thus a convenient approach is to determine the comparative optical properties of the target specimen probe volume relative to one or more reference sample probe volume(s). For example, a group of molecules of a first type (first target specimen) occupy a portion of a target specimen probe volume. A solution of a group of molecules of a second type (second target specimen) in a liquid (third target specimen) is delivered to the target specimen probe volume and then washed off. The apparatus reveals if a reaction between the first and second type of molecules has occurred by interrogating the optical properties of the target specimen probe volume which may have changed if the second type of molecules have occupied part of it by binding to the first type of molecules. Known apparatuses and methods for performing this comparison often involve the use of multiple measurements, multiple separate probe beams, complex apparatuses for scanning or changing probe beam positions, or other relatively complex approaches to realize the multiple comparative measurements.

STATEMENT OF THE INVENTION

Using a suitably formatted probe beam according to the invention, the comparison can be performed conveniently using, for example, a single source beam and a single measurement. A target specimen probe volume X, and reference sample probe volumes A and/or B, may be exposed in parallel to the formatted probe beam. The result produced is a simultaneous comparison of the optical properties of target specimen probe volume X and the optical properties of reference sample probe volumes A or B. This is but one example of the use of the formatted probe beam of the invention for comparing optical properties of probe volumes. In the formatted probe beam of the invention, a single optical source beam may be converted by passive optical elements to a pair of partially sheared probe beams formatted in multiple completely sheared probe beam pairs. The target specimen probe volumes and reference sample probe volumes are arranged in a known grid array and blanket exposed to the multiple completely sheared probe beam pairs. After exposure the multiple beams of the completely sheared beam pairs are recombined, producing interference patterns that reveal relationships between the optical properties of selected probe volumes in the grid array.

The formatted probe beam according to the invention has the unique property that it contains a partially sheared probe beam pair that is formatted into an array of completely sheared probe beam pairs. The partially sheared probe beam pair is defined as comprising two beams, a first partially sheared probe beam and a second partially sheared probe beam, wherein the first and second beams partially overlap. A completely sheared probe beam pair is defined as comprising two beams that are portions of the same partially sheared probe beam pair, the first completely sheared probe beam and the second completely sheared probe beam, with the first beam and the second beam spaced apart laterally with no overlap. Reference herein to a formatted probe beam means generically the optical beam throughout the apparatus, i.e., the source beam, the formatted beam comprising the partially and completely sheared probe beam pairs, and the combined beam in the detection region.

For the purpose of defining the invention, a formatted optical beam is defined as having partial shear. That allows the formation of an optical beam having a sheared beam pair with partial overlap and also multiple sheared beam pairs with no overlap.

BRIEF DESCRIPTION OF THE DRAWING

The invention may be better understood when considered in conjunction with the drawing in which:

FIG. 8 is a diagram of the array of interrogating elements at the source region of the formatted probe beam;

FIG. 9 is a diagram of the array of interrogating elements in the partially sheared region of the formatted probe beam;

FIG. 10 is a diagram of the array of interrogating elements in the combined region of the formatted probe beam;

FIG. 11 is a diagram of the array of interrogating elements at the detection region of the formatted probe beam;

FIG. 12 is a diagram showing a grid array of potential sites for target specimen probe volumes and reference sample probe volumes organized in the partially sheared region of the formatted probe beam;

FIG. 13 is a diagram similar to that of FIG. 12 showing alternative sites;

DETAILED DESCRIPTION OF THE INVENTION

Figure 1:
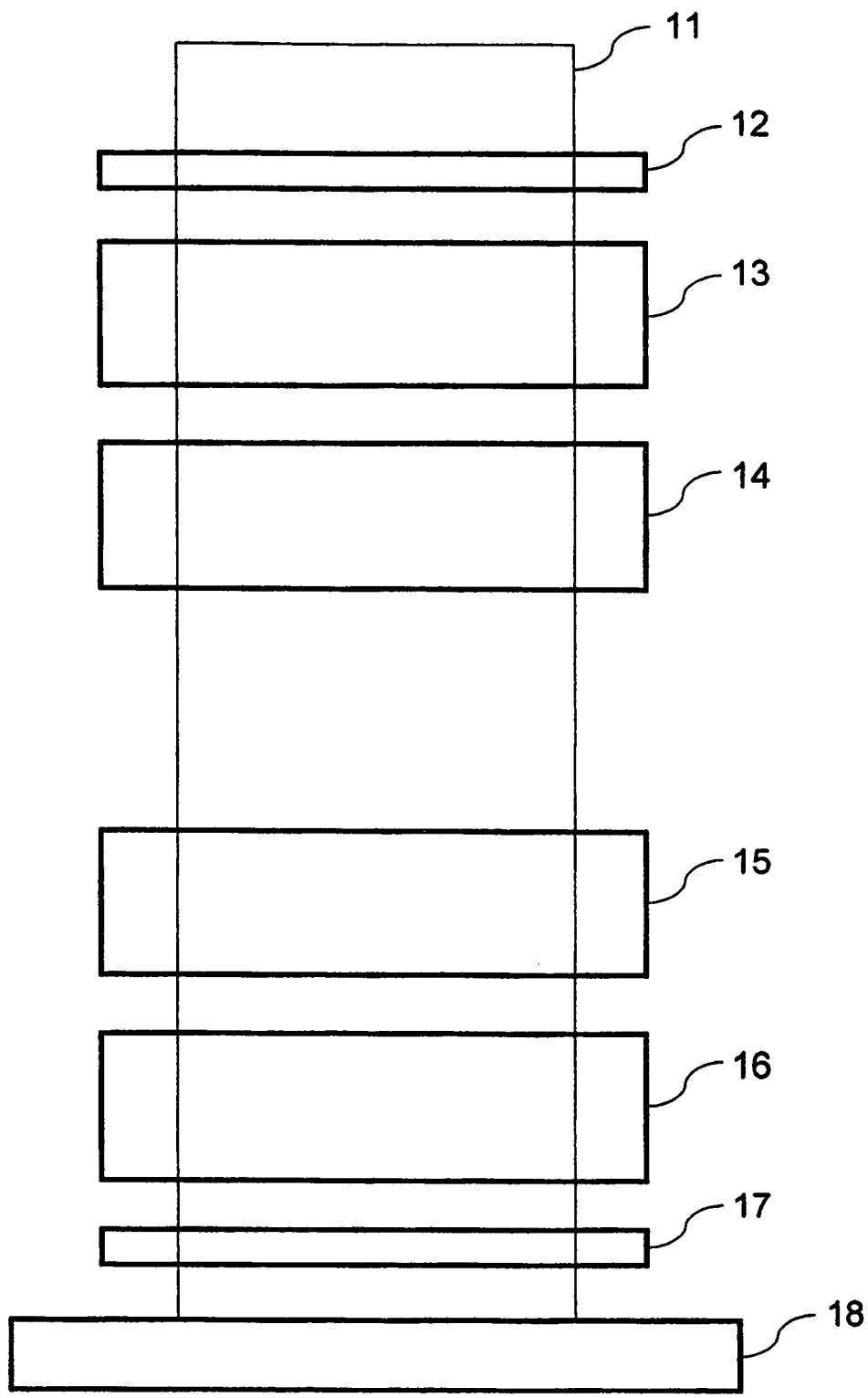
FIG. 1 is a schematic diagram showing the optical elements used to form a partial shear formatted optical probe beam according to a first embodiment of the invention.

FIG. 1 is a schematic arrangement of components for producing the partial shear formatted probe beam according to one embodiment of the invention. The formatted probe beam is represented at 11 and in the illustration simply illustrates the direction of the formatted probe beam through the various elements 12 to 18. It should be understood that the blocks 12 to 18 represent the optical elements described and are not illustrative of the size or physical characteristics of those components. Also, the elements may be spaced from one another, but are preferably in proximity in an integrated optical assembly as will be illustrated in more detail below. In the apparatus of FIG. 1 the probe beam, as it is formatted, undergoes splitting and displacement of the split beams. Accordingly the line 11 indicates only a general direction of the probe beam through the various elements in FIG. 1.

The apparatus may be operated with 11 oriented either vertically, as suggested by the figure, or horizontally. Alternatively, 11 may be both vertical and horizontal, with the beam reflected or refracted from one to the other between the source region and the detection region.

The initial source of the probe beam (not shown) may be an approximately planar optical beam source having low spatial coherence and low temporal coherence. It may be an LED, a laser, or any other source of light suitable for interrogating at least one target specimen probe volume.

Element 12 in FIG. 1 is a beam polarizer for polarizing the source beam into a polarized beam that can be divided in two components. The components are designated, for convenience, as beam E (extraordinary beam) and beam O (ordinary beam). The optical elements shown schematically in FIG. 1 are preferably optically transparent to the source beam and operate by transmission. However, equivalent functions may be obtained using suitably arranged refractive or reflective optical elements, or with combinations of refractive and reflective elements.

Element 13 is a birefringent crystal (BC) with a birefringent axis tilted with respect to direction 11. The effect of element 13 is to laterally displace the propagation direction of beam E, while maintaining it preferably parallel to the direction 11, and leaving the propagation direction of beam O unaffected. The displacement (not illustrated in FIG. 1) is referred to herein as shear. Shear is intended to mean movement of a subject axis from on-axis to an off-axis, where the on-axis is preferably parallel to the off-axis but displaced with respect to it. The amount of displacement is dependent on the shape of element 13, the tilt angle, and the optical properties of the birefringent device. The properties and operation of birefringent devices are well known and need not be addressed here.

In FIG. 1, and in subsequent figures, the birefringent device may be referred to as a "BC" or birefringent crystal. However, it could be a birefringent glass or polymer or suitably structured material. A variety of birefringent devices are known. Any suitable birefringent device may be used for formatting the probe beam according to the invention. It is only necessary to produce shear of the E beam with respect to the O beam. (It will be understood by those skilled in the art that E beams and O beams are interchangeable in this description as long as the interchange is made consistently.)

The probe beam then traverses a second BC 14. The second BC has an optic axis that lays on a plane that is parallel to the direction 11 and is orthogonal to the plane where the optic axis of the first BC lays. The function of BC 14 is to shear the O beam with respect to the E beam in a manner similar to that described in connection with BC 13. It is preferred that the shear produced by BCs 13 and 14 are the same so that a uniform offset is produced in both lateral directions. (If the direction of 11 is the z-direction, BC 13 may offset beam E in the x-direction, while BC 14 offsets beam O in the y-direction.) However, the offsets may be different.

Likewise, although it is preferred that the BC 13 and 14 have optic axes that lay in planes that are parallel to the direction 11 and are orthogonal to one another, so that the displacements occur in the x- and y-directions, deviations from being parallel to the direction 11 or orthogonal to one another may still result in a useful device.

The probe beam is now in the partial shear format region and contains optical beam pairs which are partially sheared and partially overlap and optical beam pairs that are completely sheared and do not overlap. The probe beam in this state is referred to here as having a partial shear format.

The partially sheared beam pairs and the completely sheared beam pairs of the formatted probe beam propagate through the target specimen probe volumes and the reference sample probe volumes and can intersect a target specimen carrier. The carrier may have a variety of forms including simply an imaginary plane, i.e. the target specimens and the reference samples may be in space. More typically the target specimens and the reference samples will be mounted on a transparent plate. The materials being analyzed may be contained in sample containers such as glass or plastic ampoules.

After propagating through the target specimen probe volumes and reference sample probe volumes, the partially sheared beam pairs and the completely sheared beam pairs of the formatted probe beam are combined to produce interference patterns indicative of the optical properties of the target specimen probe volumes and the reference sample probe volumes. This is conveniently achieved by subjecting the formatted beam to the reverse function of the optics that formatted it. Thus the beams traverse BCs 15 and 16, each with the optic axis suitably oriented.

The combined beam, now an array of interference patterns, after passing through a polarizer 17, is "read" by detector array 18. The detector array may be any form of imaging device that functions to reveal and/or record the interference patterns.

Figure 2:
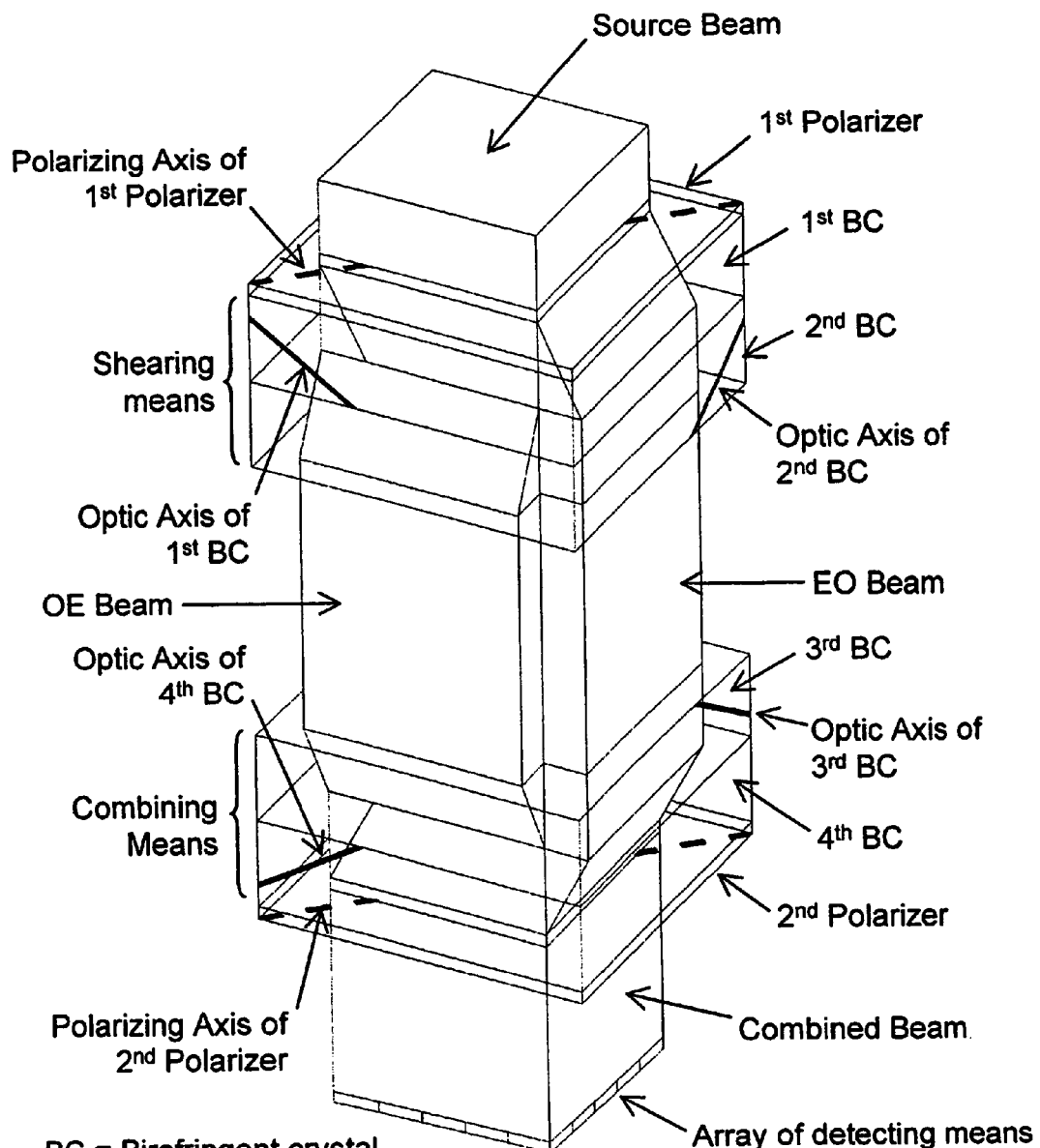
FIG. 2 is a perspective view of an apparatus constructed with the elements of FIG. 1.

An arrangement of elements like those described in FIG. 1 is shown in perspective in FIG. 2, being one embodiment of the partial shear interrogation apparatus. It comprises: a first polarizer, means to partially shear the source beam by amplitude division, hereinafter referred to as "shearing means", into a partially overlapping and relatively parallel pair of probe beams in a first and a second orthogonal polarization states, hereinafter referred to as "OE beam" and "EO beam", respectively, means to substantially combine said OE beam and EO beam into a combined beam, hereinafter referred to as "combining means", a second polarizer with its polarizing axis substantially parallel to the polarizing axis of the first polarizer and a detecting means.

As one embodiment of the shearing means, it comprises a first shearing module comprising two substantially identical birefringent crystals (BC) with their optic axis at an angle greater than zero with respect to their entrance and exit faces and with their principal sections crossed at substantially 90°.

As one embodiment of the combining means, it comprises: a second shearing module, preferably of the same configuration as the first shearing module but in any case providing an equivalent function, rotated substantially 180° with respect to the first shearing module.

The following table lists an example of the design parameters for the embodiment shown in FIG. 2.

TABLE 1

| Light source | Bare LED |
| --- | --- |
| Size of the light source | ~0.5 mm × ~0.5 mm |
| Center wavelength of the light source | ~600 nm |
| Full width at half maximum of the light source | ~30 nm |
| Distance between the light source and the $1^{st}$ polarizer | ~45 mm |
| Size of the source beam | ~10 mm diameter |
| Birefringent crystal (BC) | $YVO_4$ with a walk-off angle of ~6° |
| Size of each BC | ~10 mm × ~10 mm × ~0.5 mm |
| Size of each polarizer | ~10 mm × ~10 mm × ~0.15 mm |
| Gap between the $1^{st}$ polarizer and the $1^{st}$ BC | in proximity |
| Thickness of the shearing means (comprising the $1^{st}$ and the $2^{nd}$ BCs) | ~1.00 mm |
| Size of the effective shear | ~70 μm (each BC's shear size is ~50 μm) |
| Gap between the shearing means and the combining means | ~2.5 mm |
| Thickness of the combining means (comprising the $3^{rd}$ and the $4^{th}$ BCs) | ~1.00 mm |
| Gap between the $2^{nd}$ polarizer and the $4^{th}$ BC | in proximity |
| Gap between the $2^{nd}$ polarizer and the detecting means | ~0.7 mm |
| Size of the array of detecting means | ~3.5 mm × ~4.5 mm |
| Size of each detecting means | ~2.8 μm × ~2.8 μm |

Figure 3:
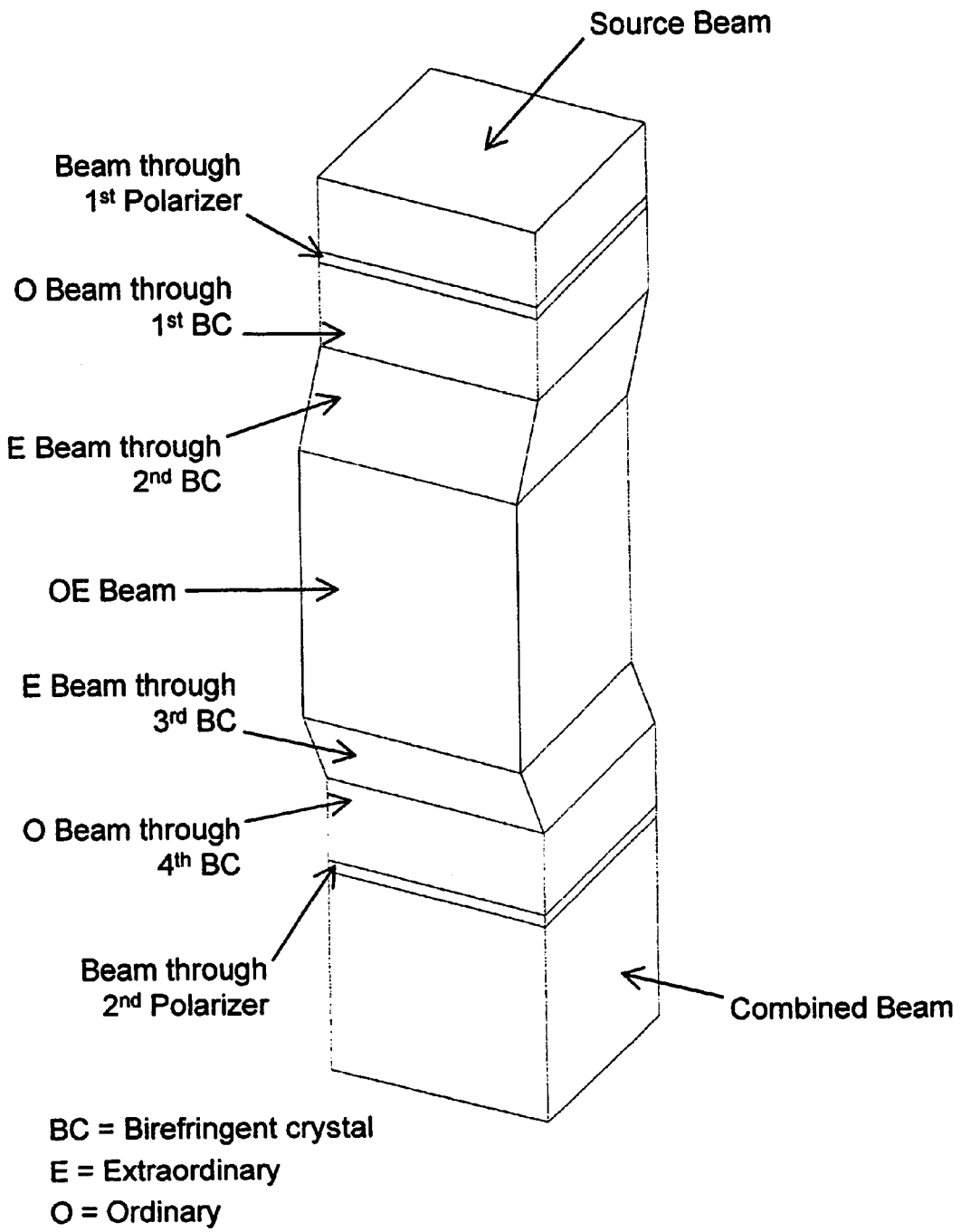
FIG. 3 is a perspective view of a component of the formatted probe beam traversing the apparatus of FIG. 2 illustrating the partially sheared probe beam, OE beam, in a first polarization state.
Figure 4:
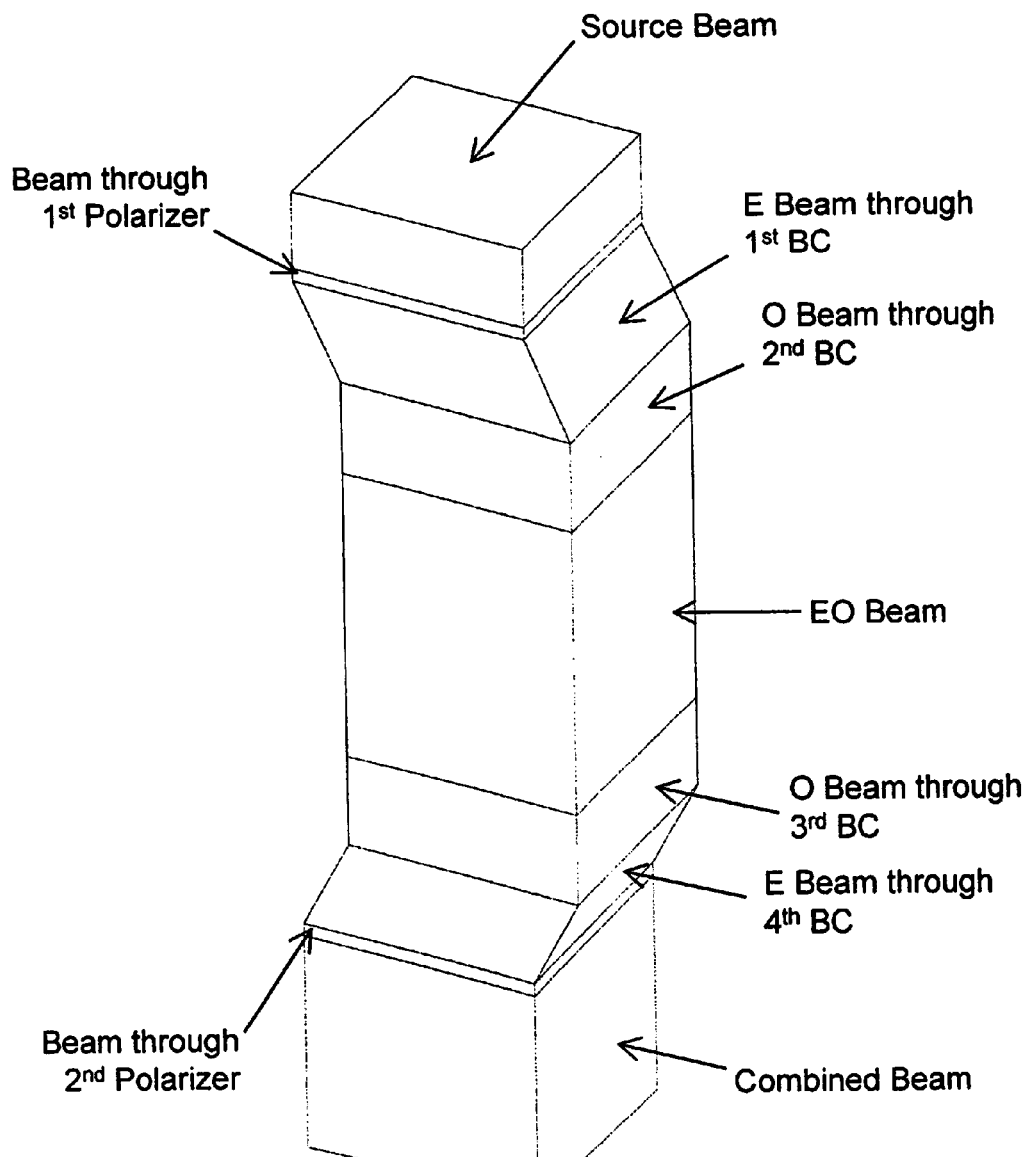
FIG. 4 is a perspective view of a component of the formatted probe beam traversing the apparatus of FIG. 2 illustrating the partially sheared probe beam, EO beam, in a second polarization state.
Figure 5:
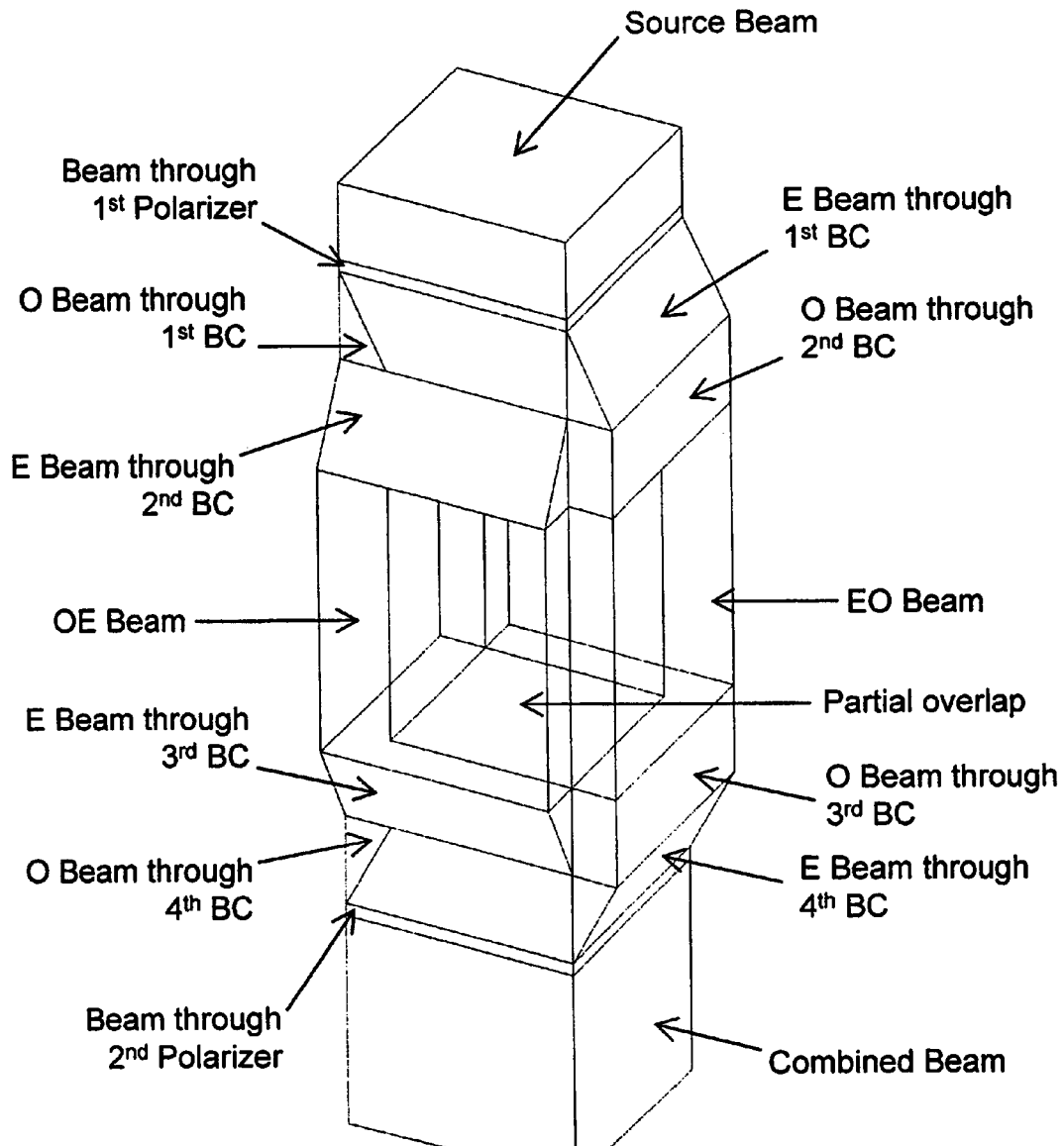
FIG. 5 shows the combination of the components of the formatted probe beam of FIGS. 3 and 4, showing the partially sheared probe beam pair, OE beam and EO beam.

For clarity, the two components of the formatted probe beam of the partial shear interference apparatus of FIG. 2 are shown separately in FIGS. 3 and 4, and comprise the source beam, the E and O beams through the BCs and the polarizers, the partially sheared probe beam pair, OE beam and EO beam, and the combined beam. Also for clarity, the partial overlap between the OE beam and the EO beam is shown in FIG. 5.

The source beam, as shown in FIG. 2, is partially sheared by the shearing means into the OE beam and the EO beam which partially overlap and propagate through the volume in between the shearing means and the combining means. The two beams are then combined by the combining means into the combined beam. Upon combining and passing through the second polarizer, the two beams interfere and produce an interference pattern that reveals the optical properties of the volume in between the shearing means and the combining means. The interference pattern is detected by the array of detecting means.

In the embodiment shown in FIGS. 2-4 the OE beam and the EO beam are shifted with respect to the source beam along the directions of the shear introduced by the second BC and the first BC, respectively. Because the directions of the shear introduced by the first BC and the second BC are perpendicular, the shearing means introduces an "effective shear" which is √2 the size of the shear introduced by either BC and along a direction at approximately 45° with respect to the direction of either shear.

The cross section of the source beam in FIGS. 2-4 is shown as square. However, optical beams of any suitable shape may be used in the invention. Typically the optical beam cross section will be quadrilateral. However, it may be round or oval, or another useful shape.

Figure 6:
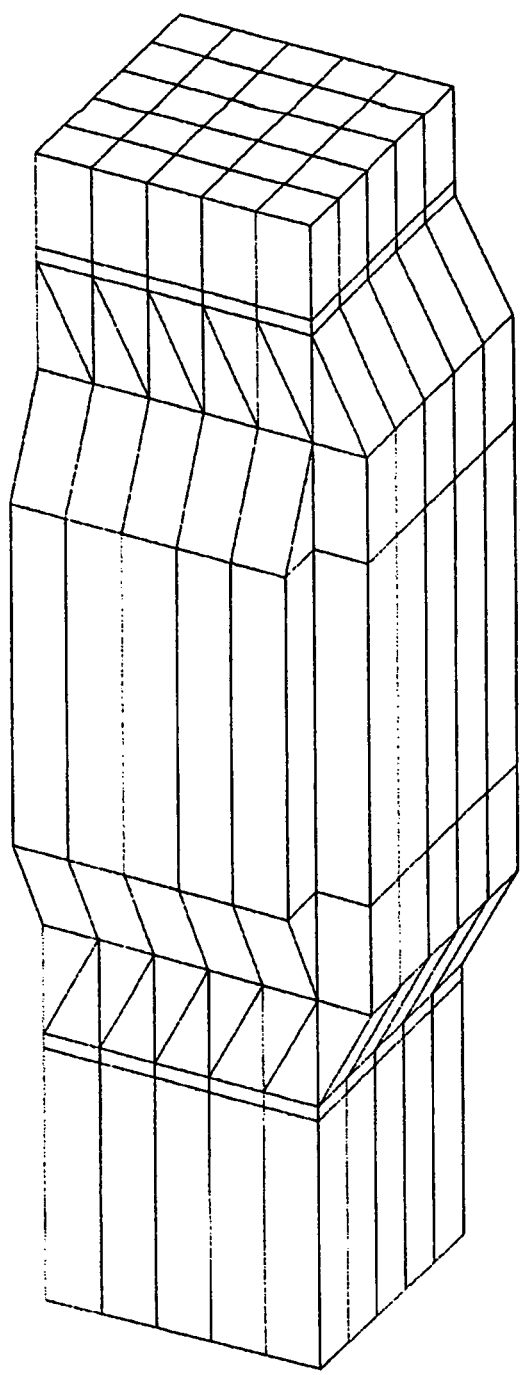
FIG. 6 illustrates schematically the formatting of the optical beam of FIG. 5 into an array of 25 interrogating elements characterized by complete shear according to one example of a possible interrogation array.

In one embodiment, as shown in FIG. 6, the source beam can be considered equivalent to an array of sub-source beams that have a square cross section with a size that, in the shear direction, matches the size of the shear, and are sheared by the shearing means into an array of completely sheared probe beam pairs, hereinafter referred to as sub-OE beams and sub-EO beams, which are then combined by the combining means into an array of sub-combined beams. Each completely sheared probe beam represents a site for a target specimen probe volume or a reference sample probe volume.

FIG. 6 shows an array of 5×5 sub-source beams that will accommodate 25 completely sheared probe beam pairs. It will be understood that in the formatted section of the apparatus each completely sheared probe volume pair is represented by a corresponding pair of completely sheared probe beams. The array may be of any suitable size. Recognizing that the formatted region of the beam has no inherent divisions, the 5×5 array is mainly a matter of choice. It reflects the area of the beam devoted to each interrogation site, and the number of interrogation sites the apparatus is designed to interrogate in a single interrogating step or in a single interrogation step of a sequence of steps. The size and shape of the 25 completely sheared probe volume pairs in FIG. 6 are the same. However, the array may contain any arrangement of probe volume pairs, each with the same or different shape and/or size.

As is evident from the figure, the size of shear of one partially sheared probe beam with respect to the other will determine the ratio of the area of overlap to the total area of the beam. That ratio may vary widely depending on the interrogation application. However, in a typical method and apparatus according to the invention that area ratio will be preferably greater than 25%.

Figure 7:
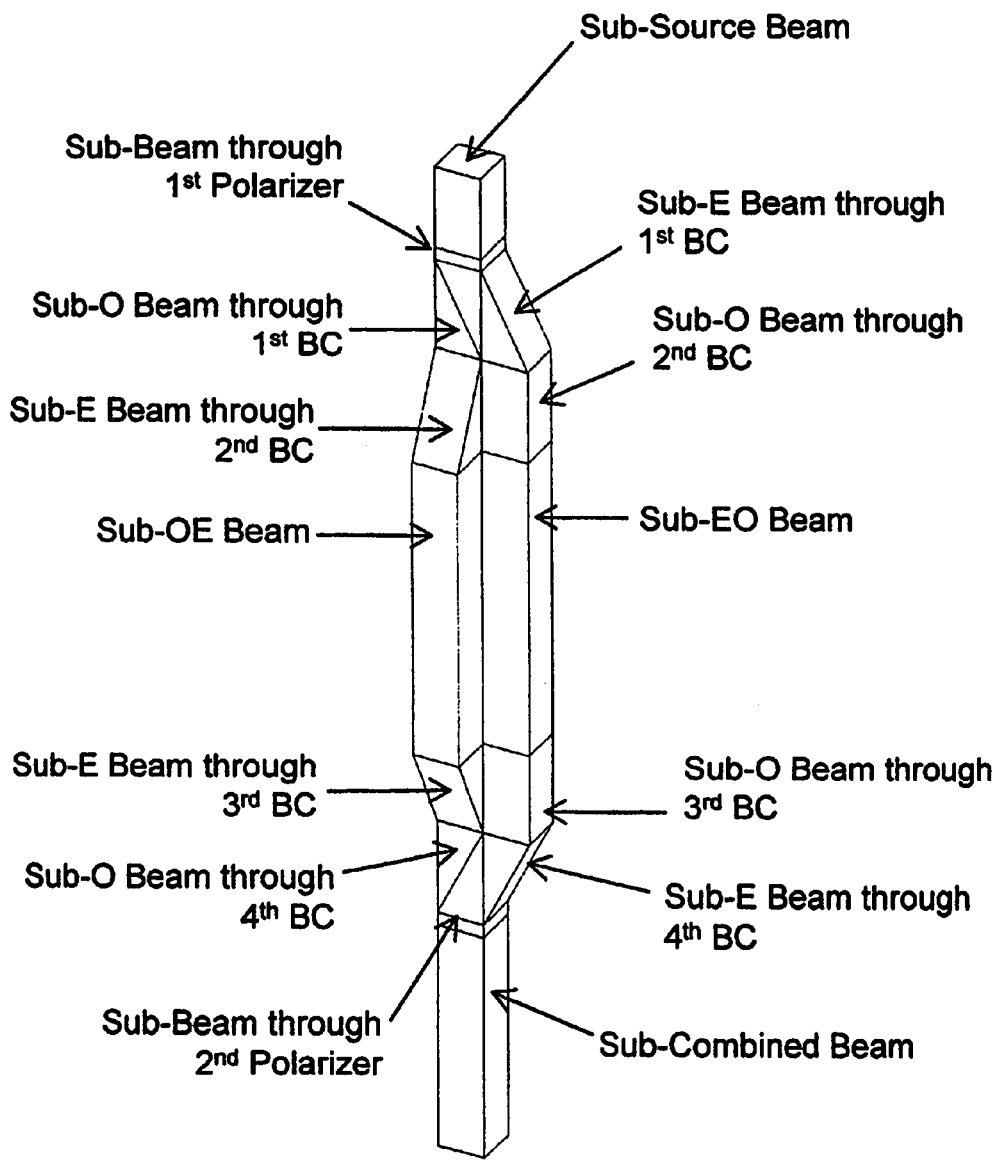
FIG. 7 shows one of the interrogating elements of FIG. 6 showing the completely sheared probe beam pair, sub-OE beam and sub-EO beam.

FIG. 7 shows one sub-source beam isolated from the array. It is clear that the corresponding completely sheared probe beam pair, sub-OE beam and sub-EO beam, do not overlap and they propagate through two separate regions of the volume in between the shearing means and the combining means. In the embodiment shown in FIG. 2, the invention de facto makes the partial shear interference apparatus function as a complete shear interference apparatus for the isolated sub-source beam and, therefore, as an array of complete shear interference apparatuses for the array of sub-source beams.

In the embodiment shown in FIG. 2, the invention dedicates a single detecting means to the detection of the interference output from each complete shear interference apparatus, and de facto makes the partial shear interrogation apparatus function as an array of complete shear interrogation apparatuses that interrogate the optical properties of the array of either of said two separate regions of the volume as compared to the array of the other region. In other words, either of the two separate regions can be a target specimen probe volume or a reference sample probe volume.

FIG. 8 shows the map of the array of sub-source beams. The array of sub-source beams corresponds to the array of completely sheared probe beam pairs in the apparatus. FIG. 9 shows the map of the array of completely sheared pairs of sub-OE beams and sub-EO beams in the formatted probe beam. FIG. 10 shows the map of the array of sub-combined beams. FIG. 11 shows the map of the array of detecting means.

The invention provides a single partial shear interference apparatus comprising a single shearing means, and a single combining means, yet it provides an array of complete shear interference apparatuses whose interference outputs are detected by an array of detecting means to interrogate an array of target specimen probe volumes as compared to an array of reference sample probe volumes.

Because of the partial overlap between the OE and the EO beams, some sub-OE beams overlap with some sub-EO beams. For example, the sub-beam OE(3,3) overlaps with the sub-beam EO(2,2) as can be seen in FIG. 9. Therefore, a target specimen probe volume that falls within the overlap between the OE and EO beams can be interrogated as compared to two reference sample probe volumes.

Figures 12, 13:
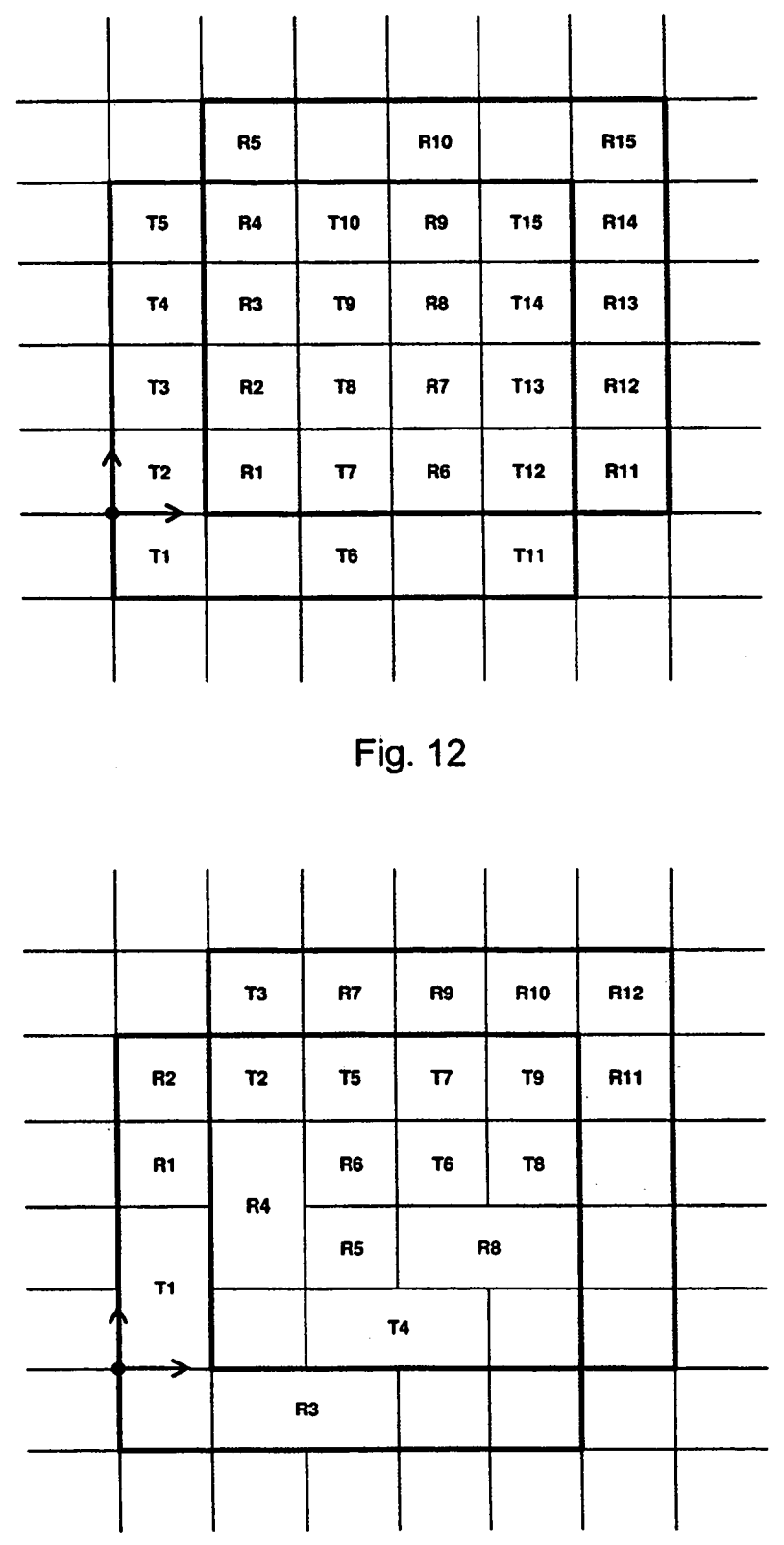

This feature of the invention can be explained with the aid of FIG. 12 which shows the map of an example of an array of target specimen probe volumes and an array of reference sample probe volumes Ti and Ri, respectively, with i=1 to 15. The target specimen probe volume T8 can be interrogated as compared to the reference sample probe volume R1 with the EO(2,2) and OE(2,2) sub-beams of FIG. 9 propagating through the target specimen probe volume and the reference sample probe volume, respectively, and also as compared to the reference sample probe volume R8 with the OE(3,3) and EO(3,3) sub-beams of FIG. 9 propagating through the target specimen probe volume and the reference sample probe volume, respectively. The two pairs are combined in the sub-combined beams C(2,2) and C(3,3) of FIG. 10 which are detected by two detecting means D(2,2) and D(3,3) respectively, of FIG. 11.

Similarly, a reference sample probe volume that falls within the overlap between the OE and EO beams can be used as a reference for two separate target specimen probe volumes. For example, with the aid of FIG. 9 and FIG. 12, the reference sample probe volume R7 can be used as a reference for the interrogation of the target specimen probe volume T7 with the OE(2,3) and EO(2,3) sub-beams of FIG. 9 propagating through the target specimen probe volume and the reference sample probe volume, respectively, and of the target specimen probe volume T14 with the EO(3,4) and OE(3,4) sub-beams of FIG. 9 propagating through the target specimen probe volume and the reference sample probe volume, respectively.

It should be noted that the beams propagating through the target specimen probe volume T8 of FIG. 12 are the EO(2,2) and OE(3,3) sub-beams of FIG. 9, and that the beams propagating through the reference sample probe volume R1 of FIG. 12 are the EO(1,1) and OE(2,2) sub-beams of FIG. 9, i.e. either sub-OE beams or sub-EO beams can propagate through the target specimen probe volume and the reference sample probe volume.

Some target specimen probe volumes in the example shown in FIG. 12 can be interrogated as compared to only one reference sample probe volume. For example, the target specimen probe volume T4 of FIG. 12 can be interrogated as compared to the reference sample probe volume R4 of FIG. 12 with the OE(4,1) and EO(4,1) sub-beams of FIG. 9, respectively.

Similarly, some reference sample probe volumes in the example shown in FIG. 12 can be used as a reference for only one target specimen probe volume. For example, the reference sample probe volume R13 of FIG. 12 can only be used as a reference for the interrogation of the target specimen probe volume T13 of FIG. 12 with the EO(3,5) and OE(3,5) sub-beams of FIG. 9, respectively.

By properly designing the interrogation apparatus, as illustrated here, it is possible to interrogate all target specimen probe volumes of an array as compared to at least one or two reference sample probe volumes of an array of reference sample probe volumes.

FIG. 13 shows the map of another example of an array of target specimen probe volumes and an array of reference sample probe volumes. The example shows how groups of target specimen probe volumes can be aligned to either shear direction, e.g. T2 and T3 along the shear direction of the second crystal and T5, T7 and T9 along the shear direction of the first crystal. The example also shows how target specimen probe volumes with a size that, along the direction perpendicular to either of the shear directions, is larger than the size of the shear can be interrogated, e.g. T1 which is twice the size of the shear along the shear direction of the second crystal, and T4 which is twice the size of the shear along the shear direction of the first crystal. Thus two or more detecting means may be dedicated to the detection of the interference output between the sub-OE beam and the sub-EO beam propagating through the larger target specimen probe volume and reference sample probe volume.

The example also shows how target specimen probe volumes may be contiguous without leaving sample reference probe volumes in between, i.e. T6, T7, T8 and T9, as long as there are reference sample probe volumes that can be used for the interrogation, i.e. R5, R6, R11 and R12, respectively.

The single source beam is preferably relatively planar to ensure that the sub-beams propagating through the target specimen probe volumes and the reference sample probe volumes do not cross over each other and thus interfere with each other. In general, the source beam has preferably low spatial coherence and low temporal coherence to prevent spurious interference noise. However, it can have high spatial coherence and high temporal coherence such as, for example, a laser beam.

The source beam may or may not need to be relatively polarized depending on whether or not the partial shear interference apparatus is polarization based. Some sources are intrinsically polarized, however some others, such as the sun or LEDs, are not polarized, and in such a case, a polarizer needs to be included in the partial shear interference apparatus if the source beam needs to be polarized. Accordingly a source beam and a polarizer should be regarded as equivalent to a polarized source beam and vice versa.

Figure 16:
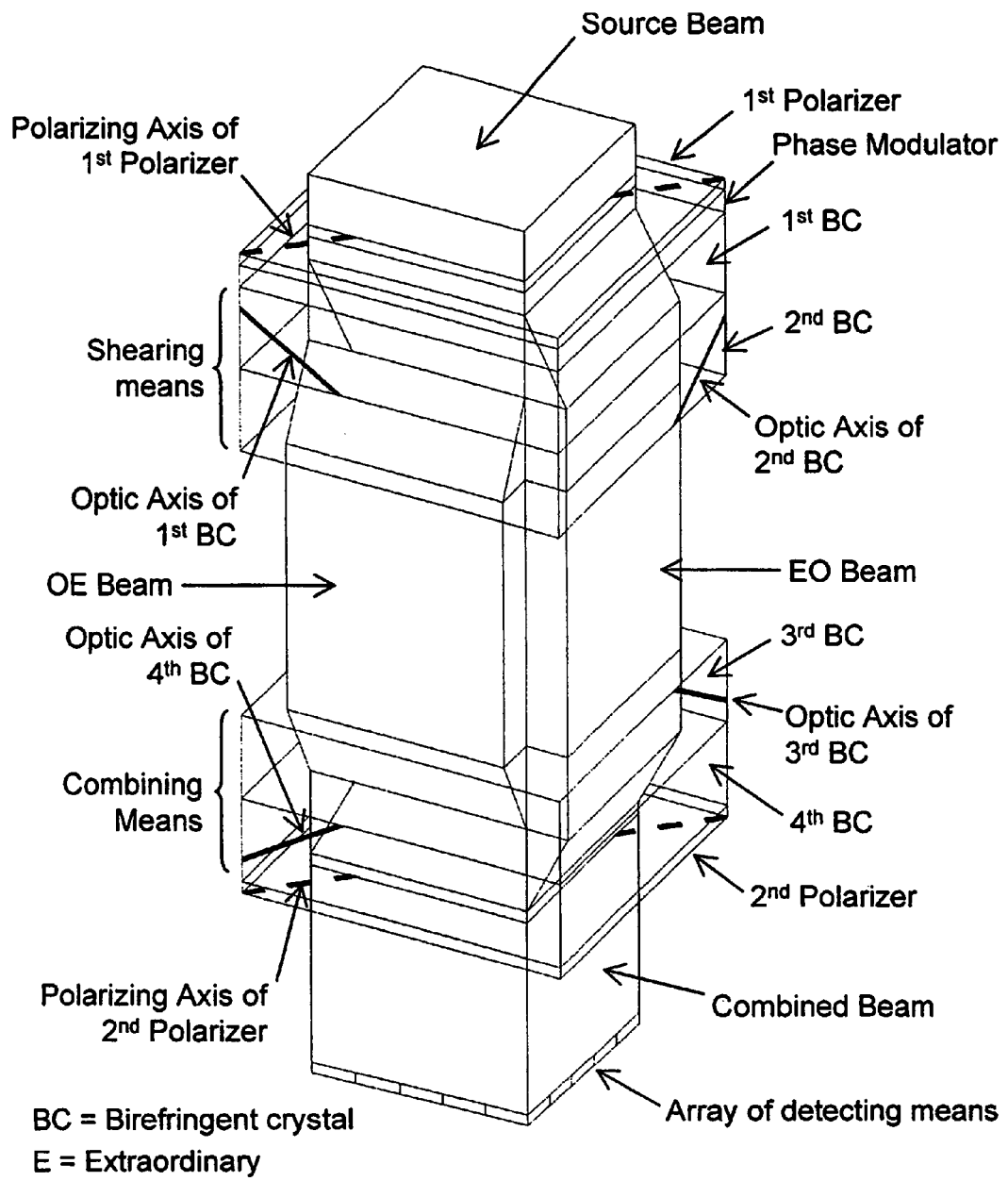
FIG. 16 is a perspective view of an apparatus similar to that of FIG. 2 with a phase modulator added.

The quantification of the optical properties of the target specimen probe volumes as compared to the reference sample probe volumes can be achieved with a technique called "phase extraction". Such a technique requires the relative phase between the sheared beams to be modulated or shifted with a phase modulator or shifter. It can be performed anywhere in the apparatus between the first polarizer and the second polarizer or between the source and the second polarizer if the source beam is polarized and there is no need for the first polarizer. For example, FIG. 16 shows a phase modulator added to the embodiment of FIG. 2 between the first polarizer and the first birefringent crystal.

Useful embodiments of the phase shifter or modulator depend on whether the shearing of the source beam is polarization based or not. They include: a liquid crystal cell, an electro-optic cell, a thermo-optic cell, a photo-elastic cell, a single mode polarization maintaining (PM) fiber wrapped around a piezoelectric cylinder, rotating a wave plate between the shearing and combining means and electro-optically or thermally tuning or mechanically tilting a birefringent crystal of the partial shear interference apparatus.

Relative phase shifting or modulation also enables the signal to noise ratio of the interrogation apparatus to be increased proportionally to the square root of the number of phase shift measurements.

Figure 17:
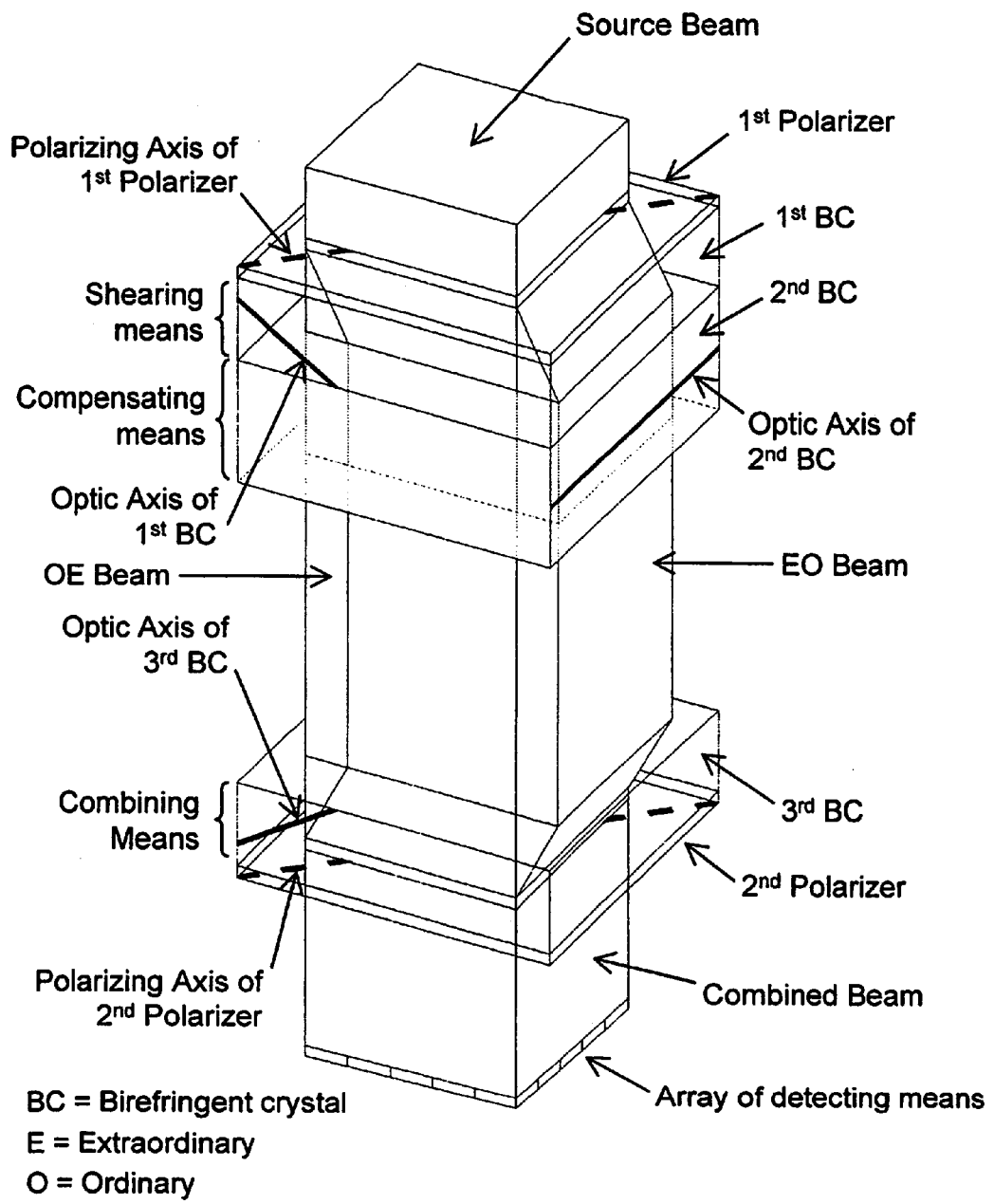
FIGS. 17 and 18 are perspective views of an alternative formatted probe beam apparatus wherein the formatted probe beam is partially sheared in one direction only.
Figure 18:
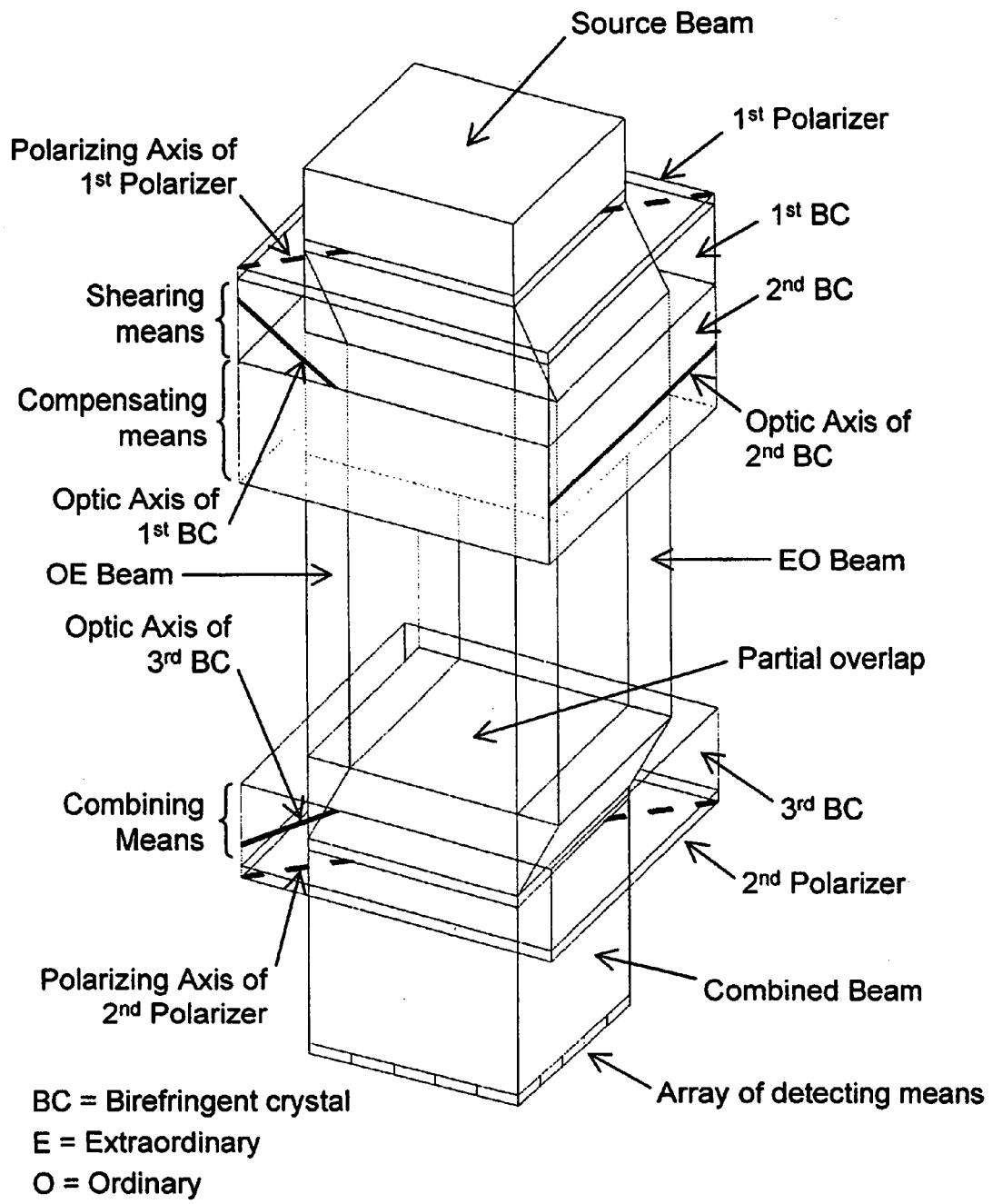

In addition to the embodiment of the interference apparatus shown in FIG. 2, other shearing means, combining means and detection means may be used in the present invention. For example, FIGS. 17 and 18 illustrate another form of partial shear apparatus. In the apparatus of FIG. 17, a partial shearing module with just a single partial shear is used, and the beam, as illustrated in FIG. 18, is displaced in a single lateral direction. This produces a formatted probe beam as described earlier, but one that has a single shear. The apparatus of FIG. 17 has three birefringent devices. The beam displacement used to produce the partially sheared probe beam pair, and the complementary displacement to combine the partially sheared probe beam pair, require only two birefringent devices. However, it will be observed that if the two birefringent crystals are of the same type, the optical paths for the two components of the formatted probe beam in FIG. 17 are different. The "optical path" in this context is the length of travel of the beam times the refractive index of the volume through which it travels. If this apparatus is used with a low coherence source, it is desirable to add a compensating means to compensate for the difference in optical path length. The compensating means in the apparatus of FIG. 17 is a third BC, whereby the beam with the shorter optical path through the apparatus "sees" an additional optical path that is longer than the optical path added to the longer optical path length. Thus the optical paths of the two beams are substantially equalized.

Figure 19:
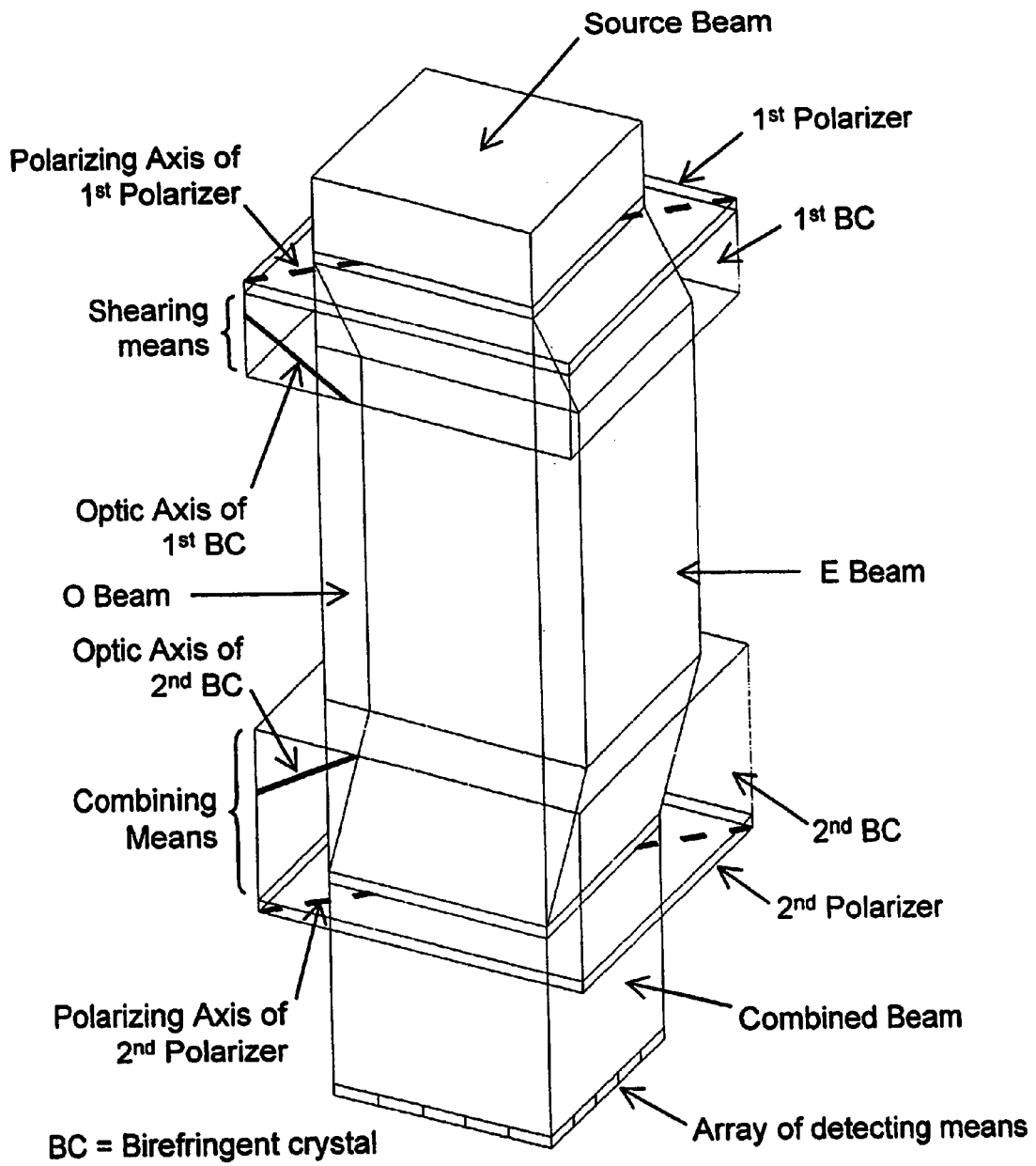
FIGS. 19 and 20 are perspective views of an alternative formatted probe beam apparatus wherein the probe beam is partially sheared in one direction only.
Figure 20:
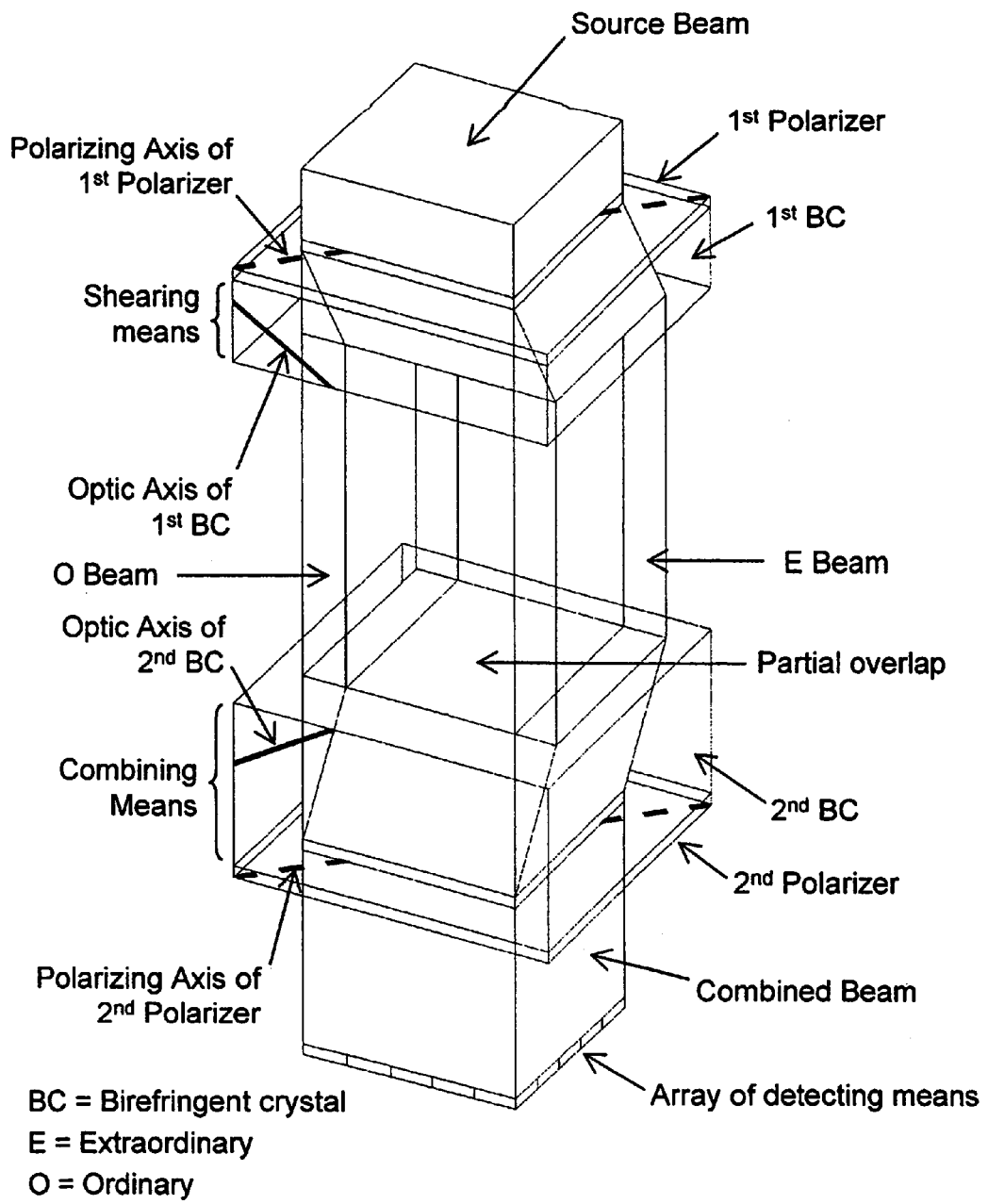

FIGS. 19 and 20 are perspective views of an alternative partial shear apparatus wherein the formatted probe beam is partially sheared in one direction only. However, the first and second BCs are of a different type, i.e. one is positive and the other is negative, or vice versa. By properly designing the two crystals, the lateral shear can be substantially matched and the optical path of the two components of the formatted probe beam can be substantially equalized.

Figure 21:
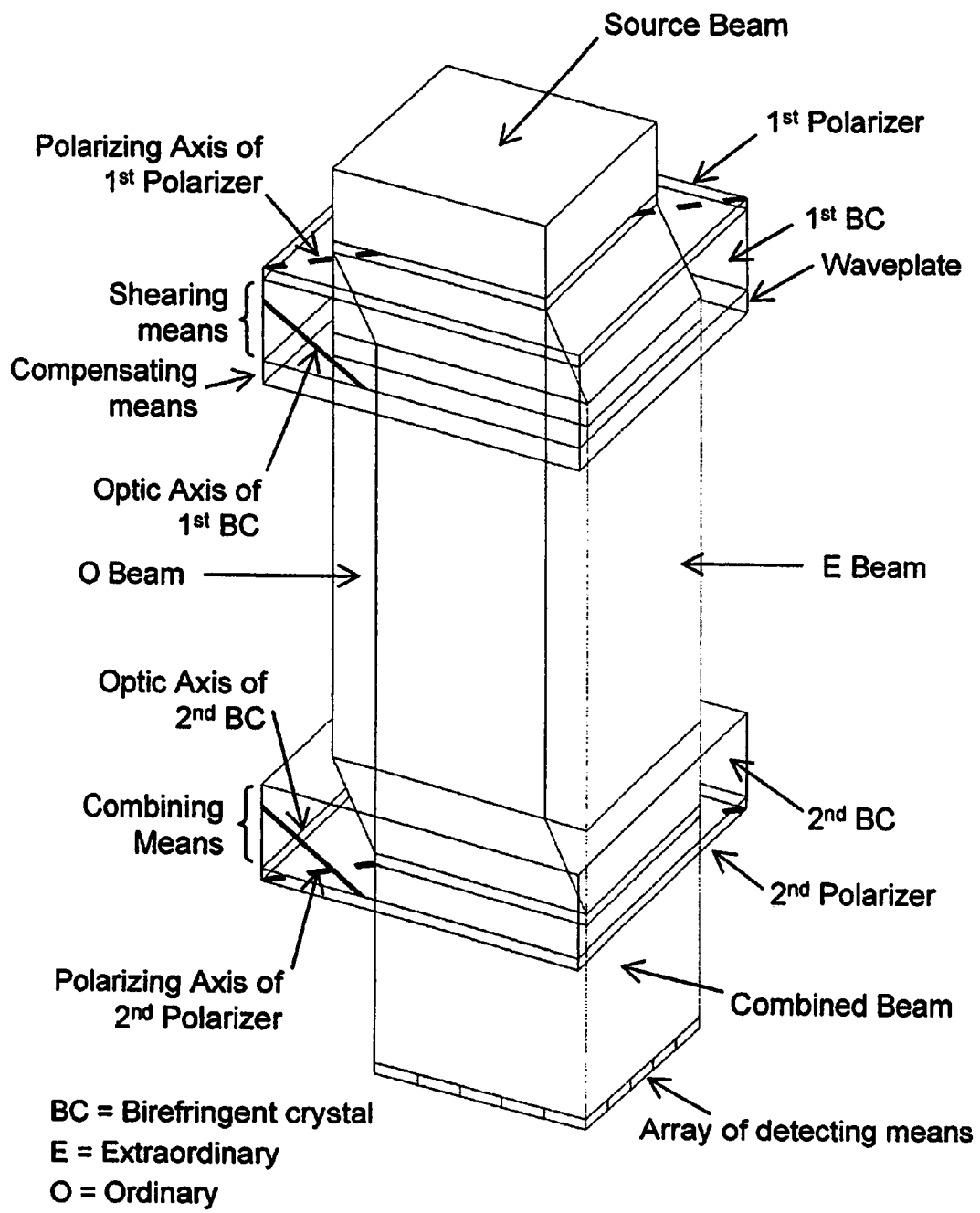
FIGS. 21 and 22 are perspective views of an alternative formatted probe beam apparatus wherein the probe beam is partially sheared in one direction only.
Figure 22:
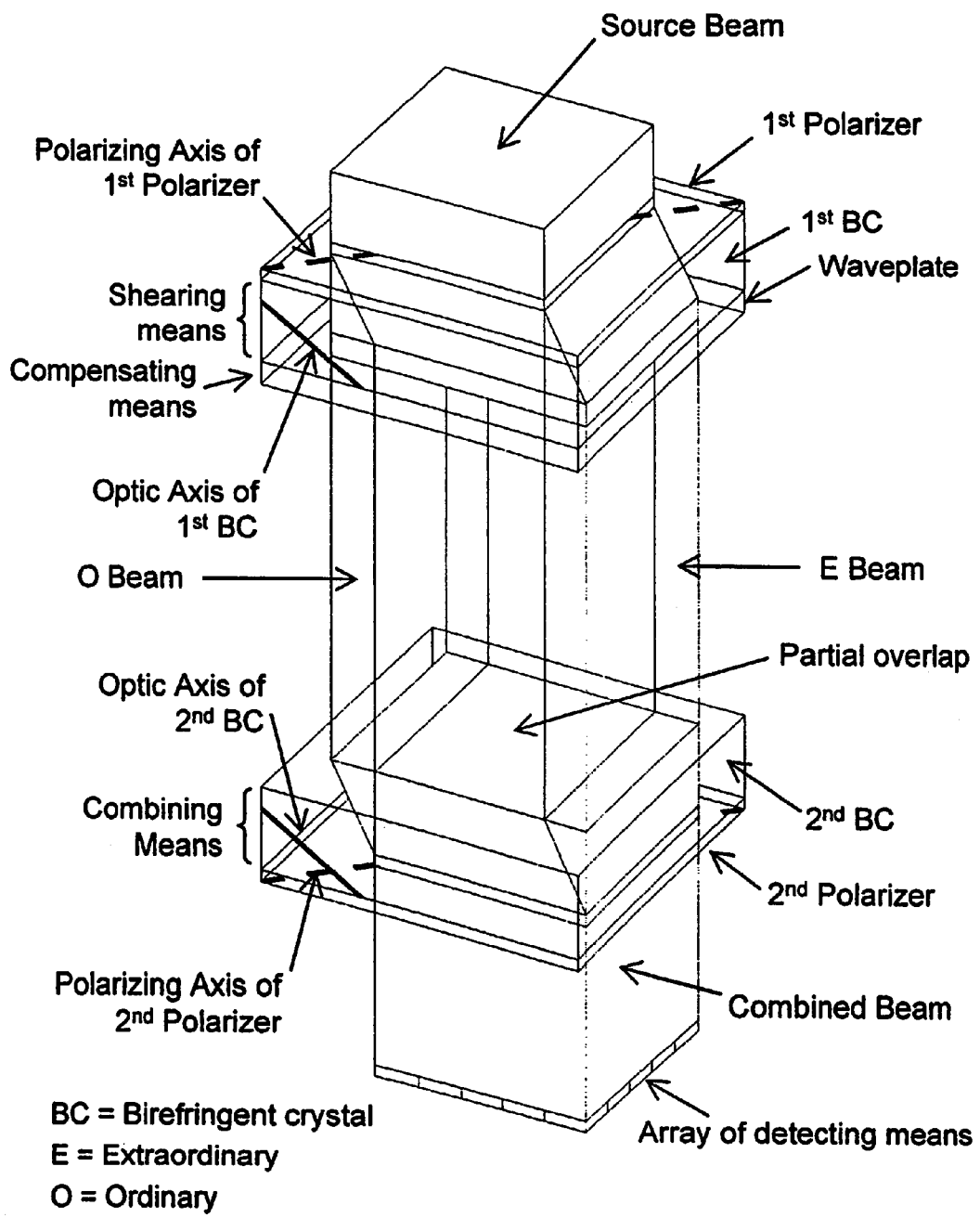

FIGS. 21 and 22 are perspective views of another alternative partial shear apparatus wherein the formatted probe beam is partially sheared in one direction only. In this case, the first and second birefringent crystals are of the same type, i.e. both are positive or negative, and are preferably made from the same wafer. A polarization rotating element such as a half wave plate or a Faraday rotator is inserted between the two crystals so that the polarization direction of each partially sheared beam is rotated by 90 degrees. As a result, the ordinary beam leaving the first crystal will enter the second crystal as an extraordinary beam, and the extraordinary beam leaving the first crystal will enter the second crystal as an ordinary beam. Accordingly, the lateral shear can be substantially matched and the optical path of the two components of the formatted probe beam can be substantially equalized.

In the embodiment shown in FIG. 2, the shearing means and the combining means inherently compensate each other in terms of the optical path length. It should be noted that a separate optical path length compensating means can be added to the interrogation apparatus and can be placed anywhere in the apparatus between the first polarizer and the second polarizer, or between the source and the second polarizer if the source beam is polarized and there is no need for the first polarizer, as long as it substantially compensates the partial shear interference apparatus. If a laser beam is used as the source beam, there is no need for the interrogation apparatus to be compensated.

The polarizing axis of the second polarizer, if required after the combining means, is preferably parallel (as shown in FIG. 2) or orthogonal to the polarizing axis of the first polarizer, if the interference apparatus requires one, or to the polarization direction of the polarized source beam. It can also be along any other direction as long as the polarizer polarizes the two orthogonal polarizations of the EO and OE beams or sub-beams.

The advantage of those embodiments that use identical birefringent crystals, as in the apparatus of FIG. 2, is that they can be made from the same wafer so that their optic axis orientation and thickness can be well matched to ensure substantial spatial realignment of the sheared beams as well as substantial equalization of the optical path of the two components of the formatted probe beam.

The birefringent crystals, in general, can have either positive or negative birefringence and be either uniaxial or biaxial.

The detecting means is any device that uses any opto-electric effect to convert electromagnetic radiant energy into an electrical signal as it is known to those skilled in the art. Detecting means indicates indifferently a single detecting means or a cluster of detecting means as long as the detecting means of a cluster are dedicated to the interrogation of the same target specimen probe volume as compared to the same reference sample probe volume.

Alternatively the detecting means may be just visual observation, if the viewer is able to identify a given pattern.

Figure 14:
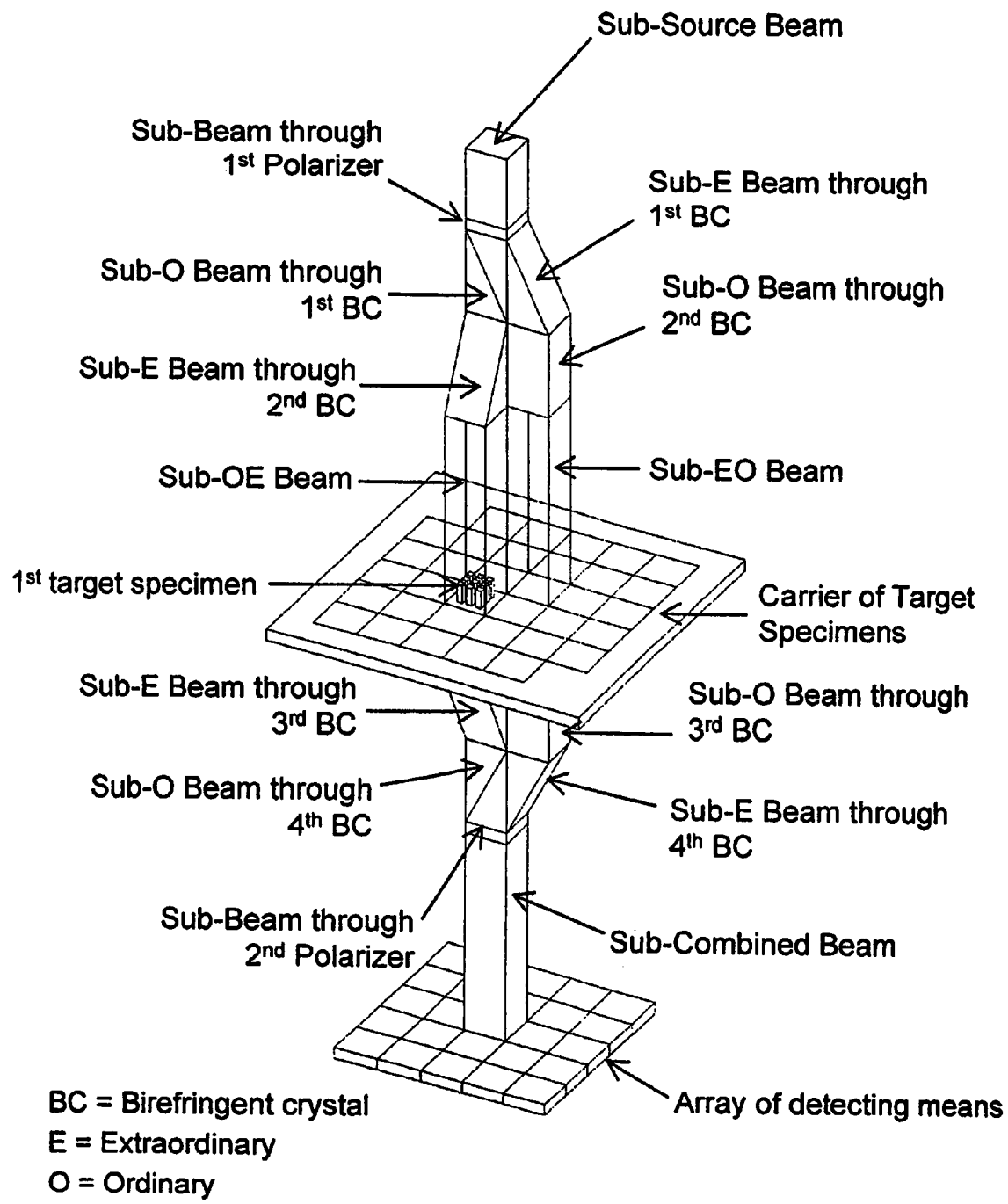
FIG. 14 is a perspective view of an individual interrogating element and a target specimen placed as shown on the target specimen carrier partially occupying the target specimen probe volume of the interrogating element.

The optical properties of the target specimen probe volumes and/or the reference sample probe volumes can be compared to produce relative measurements. For example, a group of molecules of a first type (first target specimen) occupy a portion of a target specimen probe volume (FIG. 14). A solution of a group of molecules of a second type (second target specimen) in a liquid (third target specimen) is delivered to the target specimen probe volume and then washed off. The apparatus reveals if a reaction between the two types of molecules has occurred by comparing the optical properties of the reference sample probe volume which have not changed, to the optical properties of the target specimen probe volume which may have changed if the second type of molecules have occupied a portion of the target specimen probe volume by binding to the first type of molecules (FIG. 15).

Figure 15:
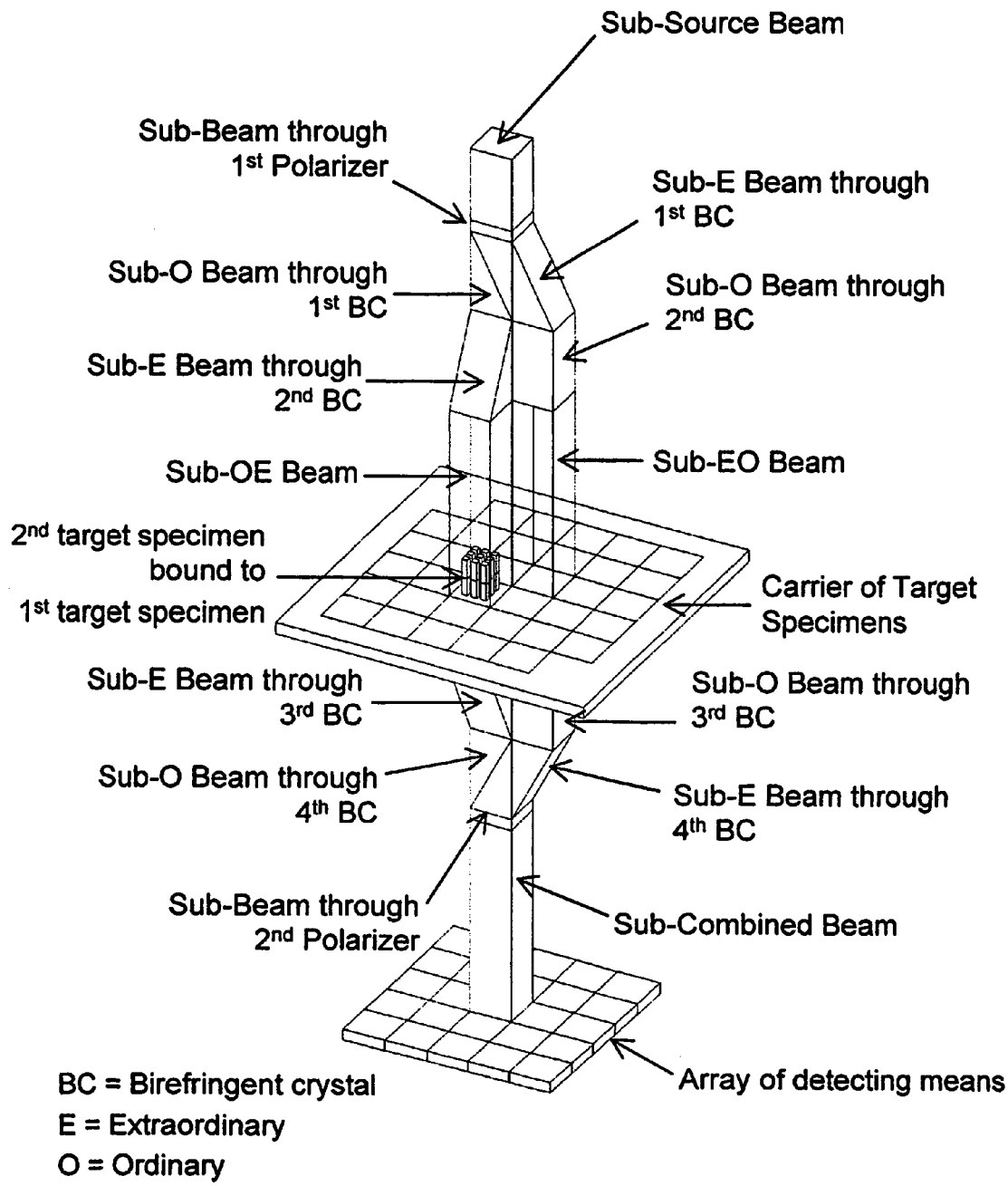
FIG. 15 is a view similar to that of FIG. 14 with a second target specimen added to the first target specimen.

In some applications it may be preferable to arrange the target specimens on a carrier, as shown in FIGS. 14 and 15, so that they can be, for example, stored together, loaded in, and unloaded from, the apparatus together. In some other applications it may be preferable to arrange the target specimens directly on a part of the apparatus.

In some applications it may be preferable to remove the target specimens from the interrogation apparatus and replace them with other target specimens. In some other applications it may be convenient to integrate some target specimens and the interrogation apparatus in a permanent fashion.

An advantage of the invention is that it interrogates the optical properties of an array of target specimen probe volumes as compared to an array of reference sample probe volumes which can be known and/or controlled independently from the target specimen probe volumes. This is particularly useful in several applications. For example, in applications that involve chemical reactions some molecules of interest can occupy the target specimen probe volumes and some the reference sample probe volumes. Control molecules known, for example, to be inert to certain events of interest, can occupy the reference sample probe volumes.

Another advantage of the invention is that it enables the optical equivalent of what in integrated electronics is generally called "common mode rejection". Because of the close proximity between the target specimen probe volumes and the reference sample probe volumes, the environmental perturbations seen by both volumes are substantially the same and, therefore, do not induce phase shift noise that would be otherwise revealed by the apparatus.

Another advantage of the invention is the range of dimensions of the target specimen probe volumes and reference sample probe volumes that it can interrogate. The invention can interrogate target specimen probe volumes as compared to reference sample probe volumes that along the direction of propagation of light can span from a few nanometers to several millimeters depending on the design and the application. This is a significant advantage when compared to those apparatuses and methods that interrogate target specimen probe volumes with evanescent fields. These typically are limited to a very narrow range of target specimen probe volumes in the order of the wavelength of the source beam.

Another advantage of the invention is that it may use a source beam with low spatial coherence and low temporal coherence. Therefore, it is relatively immune to adverse effects that highly coherent source beams, such as laser beams, typically generate. These include speckles, optical diffraction patterns, and other spurious light interference effects from, for example, undesired reflections that typically deteriorate the performance of the optical interrogation.

Another advantage of the invention is that a single phase shifter or modulator is sufficient to blanket shift or modulate the relative phase between the beams of the completely sheared beam pairs of the array of complete shear interference apparatuses.

In summary, the method and apparatus of the invention are designed to interrogate the optical properties of target specimen probe volumes as compared to the optical properties of reference sample probe volumes. The method involves dividing and shearing an optical source beam to produce a formatted optical beam comprising a first and a second partially sheared probe beams, exposing simultaneously at least one target specimen probe volume and at least one reference sample probe volume to the formatted optical beam, combining the first and second optical beam components, and detecting an interference pattern produced by the combined optical beam components.

The apparatus comprises a shearing means for dividing and shearing an optical source beam to produce a formatted optical beam comprising a first and a second partially sheared probe beams, a combining means for recombining the first and second optical beam components to produce a combined optical beam, and an optical detector for detecting an interference pattern in the combined optical beam. The definition above is intended to convey a relationship between the first and second optical beams wherein at least one of the two optical beams is sheared (displaced) with respect to the other. In the arrangement of FIG. 2, both of the divided optical beams are displaced. However, it should be understood that in useful embodiments of the invention it is only necessary for one optical beam to be displaced relative to the other beam in a manner resulting in the two optical beams having partial overlap.

In concluding the detailed description it is evident that various additional modifications of this invention may occur to those skilled in the art. All deviations from the specific teachings of this specification that basically rely on the principles and their equivalents through which the art has been advanced are properly considered within the scope of the invention as described and claimed.

The invention claimed is:

1. A method for interrogating target specimen probe volumes comprising:
    dividing and shearing an optical source beam to produce a formatted optical beam comprising a first probe beam and a second probe beam, whereby the first probe beam and the second probe beam partially overlap, wherein the formatted optical beam has a grid array of probe volume pairs,
    exposing at least one target specimen probe volume and at least one reference sample probe volume to the formatted optical beam,
    combining the first probe beam and the second probe beam to produce a combined optical beam, and
    detecting an interference pattern in the combined optical beam.

2. The method of claim 1 wherein the first probe beam and the second probe beam in the formatted optical beam are parallel.

3. The method of claim 2 wherein both the first probe beam and the second probe beam are sheared.

4. The method of claim 2 wherein the optical source beam is polarized to produce a polarized optical beam.

5. The method of claim 4 wherein the polarized optical beam is divided and sheared using at least one birefringent device.

6. The method of claim 1 wherein the grid array contains probe volume pairs wherein one of the pair is a portion of the first probe beam and the other of the pair is a portion of the second probe beam.

7. The method of claim 1 wherein the first probe beam and the second probe beam are combined using at least one birefringent device.

8. An apparatus for interrogating target specimen probe volumes comprising:
    a shearing means for dividing and shearing an optical source beam to produce a formatted optical beam comprising a first probe beam and a second probe beam, wherein the first probe beam and the second probe beam partially overlap,
    a combining means for combining the first probe beam and the second probe beam to produce a combined optical beam,
    detecting means for detecting an interference pattern in the combined optical beam and a sample carrier placed to intersect the formatted optical beam, wherein the sample carrier comprises an array of pairs of target specimens and reference samples and the detection means comprises an array of detection devices, with the array of individual detection devices corresponding to the array of pairs of target specimens and reference samples on the sample carrier.

9. The apparatus of claim 8 wherein the first probe beam and the second probe beam in the formatted optical beam are parallel.

10. The apparatus of claim 8 wherein the optical source beam is sheared in two directions.

11. The apparatus of claim 10 wherein the shearing means comprises a first birefringent device for shearing the optical source beam in a first lateral direction to produce a pair of partially sheared probe beams and a second birefringent device for shearing the pair of partially sheared probe beams in a lateral direction approximately perpendicular to the first lateral direction.

12. The apparatus of claim 11 wherein the combining means comprises a first birefringent device for shearing the formatted optical beam in a first lateral direction to produce a pair of partially sheared probe beams and a second birefringent device for shearing the pair of partially sheared probe beams in a lateral direction approximately perpendicular to the first lateral direction.

13. The apparatus of claim 8 further including an optical beam polarizer for polarizing the source beam into a polarized beam that can be divided in two components.

14. The apparatus of claim 8 wherein the optical beam source has low spatial, coherence and low temporal coherence.

15. The apparatus of claim 8 wherein the optical beam source is an LED or a laser.

16. The apparatus of claim 8 wherein the optical path length traveled by the first beam is substantially the same as the optical path length of the second optical beam.

17. The apparatus of claim 8 further comprising a compensating means for compensating or adjusting the relative optical path length of the two partially sheared optical beams.

18. The apparatus of claim 8 further comprising a phase modulator.

* * * * *

UNITED STATES PATENT AND TRADEMARK OFFICE
CERTIFICATE OF CORRECTION

PATENT NO. : 8,472,031 B2
APPLICATION NO. : 12/800873
DATED : June 25, 2013
INVENTOR(S) : Giovanni Bargarossa and Yan Zhou It is certified that error appears in the above-identified patent and that said Letters Patent is hereby corrected as shown below:

On the title page, item (73) Assignee should read as follows:

Valerio Pruneri, Castelldefels-Barcelona (ES);
Marc Jofre Cruanyes, Canet de Mar-Barcelona (ES);
Pedro Antonio Martinez Cordero, Castelldefels-Barcelona (ES); and
Davide Luca Janner, Castelldefels-Barcelona (ES).

Signed and Sealed this
Fifth Day of November, 2013

Teresa Stanek Rea
*Deputy Director of the United States Patent and Trademark Office*